United States Patent [19]

Warriner

[11] Patent Number: Plant 5,658

[45] Date of Patent: Feb. 11, 1986

[54] ROSE PLANT JACORE

[75] Inventor: William A. Warriner, Tustin, Calif.

[73] Assignee: Jackson & Perkins Co., Meford, Oreg.

[21] Appl. No.: 615,553

[22] Filed: May 31, 1984

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Manford R. Haxton

[57] ABSTRACT

A hybrid tea rose variety having abundant production of long, heavy stems bearing red buds that open to red blooms of 30–35 partially quilled petals with no fragrance, a peculiar twisting habit of growth of the peduncles.

2 Drawing Figures

This present invention relates to a new and distinct variety of rose plant of the hybrid tea class which was originated by crossing an unnamed variety with the variety Samantha, U.S. Plant Pat. No. 3,727.

The primary object of this breeding was to produce a new rose variety suitable for use in a greenhouse to produce large, long-stemmed, red cut blooms. This objective was substantially achieved along with other desirable improvements as characteristics which are outstanding in the new variety and which distinguish it from its parents as well as from all other varieties of which I am aware:

1. A vigorous plant producing an abundance of long-stemmed blooms suitable for cutting, stems being generally stronger than those of Samantha;
2. A peculiar characteristic of peduncles displaying a somewhat twisted growth until maturity when the entire stem becomes straight;
3. Thirty to thirty-five large petals;
4. Petal color similar to Samantha, U.S. Plant Pat. No. 3,727, and Showstopper, U.S. Plant Pat. No. 4,851, being red close to R.H.S. 46A on the upper side of petals and R.H.S. 53B on lower side;
5. Petal form is more curled or quilled than that of Samantha and Showstopper;
6. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:
- *Seed parent.*—Unnamed variety.
- *Pollen parent.*—Samantha, U.S. Plant Pat. No. 3,727.

Classification:
- *Botanical.*—Rosa hybrid.
- *Commercial.*—Hybrid tea.

FLOWER

Observations made from specimens grown in a greenhouse at Irvine, Calif. in April.

Blooming habit: Continuous.

Bud:
- *Size.*—Approximately 1½" when petals start to unfurl.
- *Form.*—Pointed ovoid, broad base.
- *Color.*—When sepals first divide, near Red 46A. When half blown; upper side of petals near Red Group 46A; lower side of petals near Red Group 53B.
- *Sepals.*—Color: Green 138A. Three appendaged sepals lightly appendaged. Two appendaged sepals hairy edged.
- *Receptacle.*—Color: Green 138B. Shape: Funnel. size: Large, broad. Surface: Smooth.
- *Peduncle.*—Length: Medium to short. Surface: Smooth. Color: Light green, 138B. Strength: Stiff, erect; peduncles of secondary buds sometimes bending during growth.
- *Opening.*—Spiral opening.

Open bloom:
- *Size.*—Large. Average open size 4–5".
- *Borne.*—Singly, or several together; often produces secondary buds.
- *Stems.*—Long to medium, strong.
- *Form.*—When first open, high center. Permanence: All petals curl, quill fashion.
- *Petalage.*—Number of petals under normal conditions: 30–35.
- *Color.*—Center of flower: Upper side of petals, near Red Group 46B; reverse side of petals, near Red Group 53C. Base of petals, small white area at point of attachment. Major color: Red 46B.
- *Variegations.*—Occasional white streaks on midrib of outer petals.
- *Discoloration.*—General tonality at end of first day: No change. Third day: No change; color begins to lighten in 5–6 days on the plant.
- *Fragrance.*—None.

Petals:
- *Texture.*—Thin.
- *Shape.*—Nearly round.
- *Form.*—Edges moderately quilled.
- *Arrangement.*—Imbricated, Petaloids in center, few.

*Persistence.*—Drop off cleanly.
*Lastingness.*—On the plant, long. As cut flower, long.

Reproductive parts:
*Anthers.*—Large, many. Color: Reddish purple. Arrangement: Regular around styles.
*Filaments.*—Color: Pink.
*Pollen.*—Gold yellow.
*Styles.*—Color: Reddish.
*Stigmas.*—Color: Greenish white.

PLANT

Form: Bush.
Growth: Very Vigorous, upright.
Foliage: Number of leaflets on normal mid-stem leaves: Normally 7; sometimes 5.
*Size.*—Large.
*Quantity.*—Normal.
*Color.*—New foliage: Light green, heavily overlaid with Greyed Purple 183B. Old foliage: Green 137A.

Leaflets:
*Shape.*—Broadly oval.
*Texture.*—Leathery.
*Edge.*—Serrated; slightly undulated.
*Serration.*—Single; small.

*Petiole.*—Rachis: Color: Green to reddish. Underside: Prickles.
*Stipules.*—Long, bearded.
*Disease resistance.*—Resistant to mildew, under normal growing conditions at Irvine, Calif., when observed in greenhouse conditions.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Long, straight.
*Color when young.*—Brown.

Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of its abundant production of long, heavy stems bearing red buds that open to red blooms of 30–35 partially quilled petals with no fragrance, a peculiar twisting habit of growth of the peduncles.

* * * * *

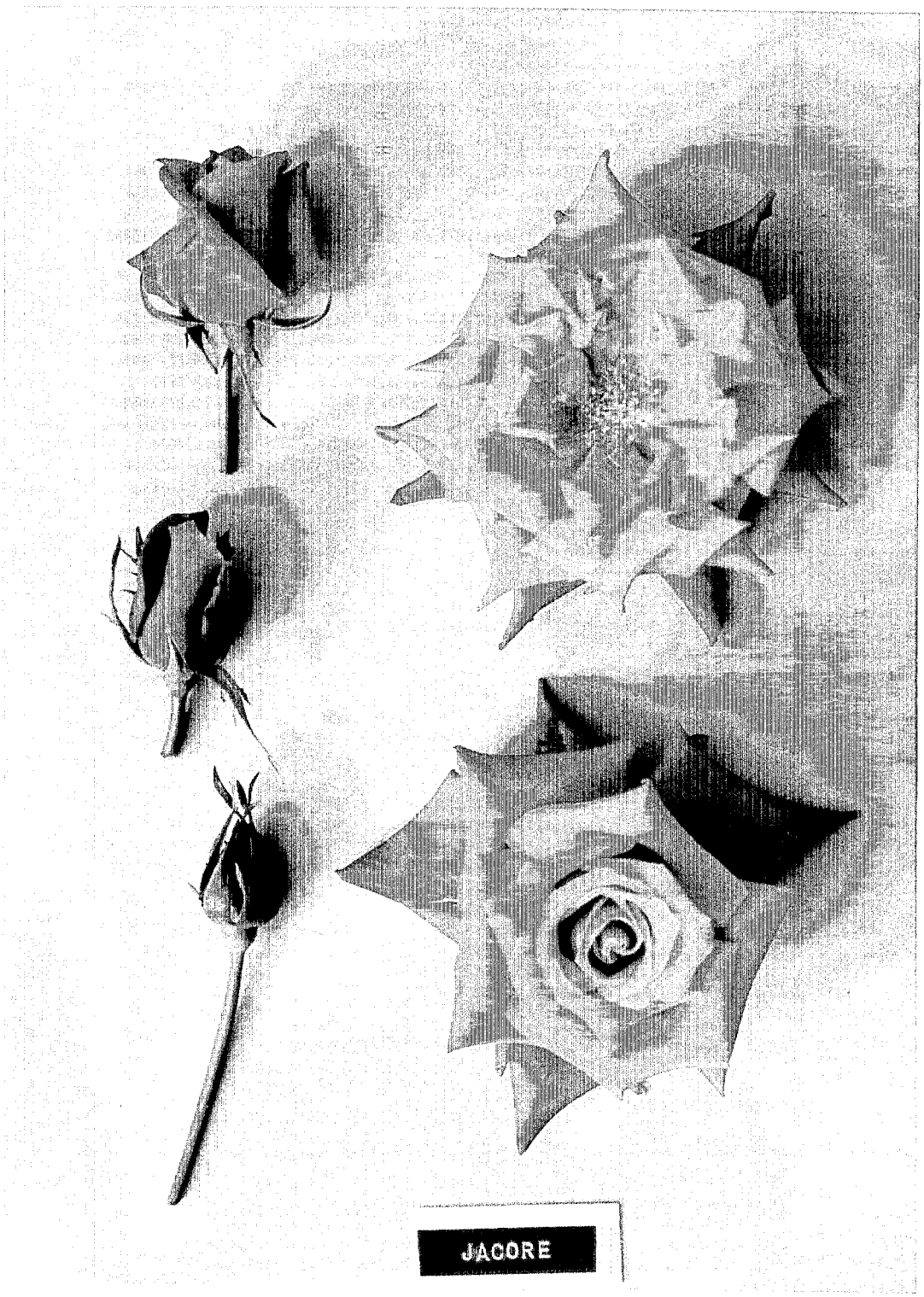
JACORE

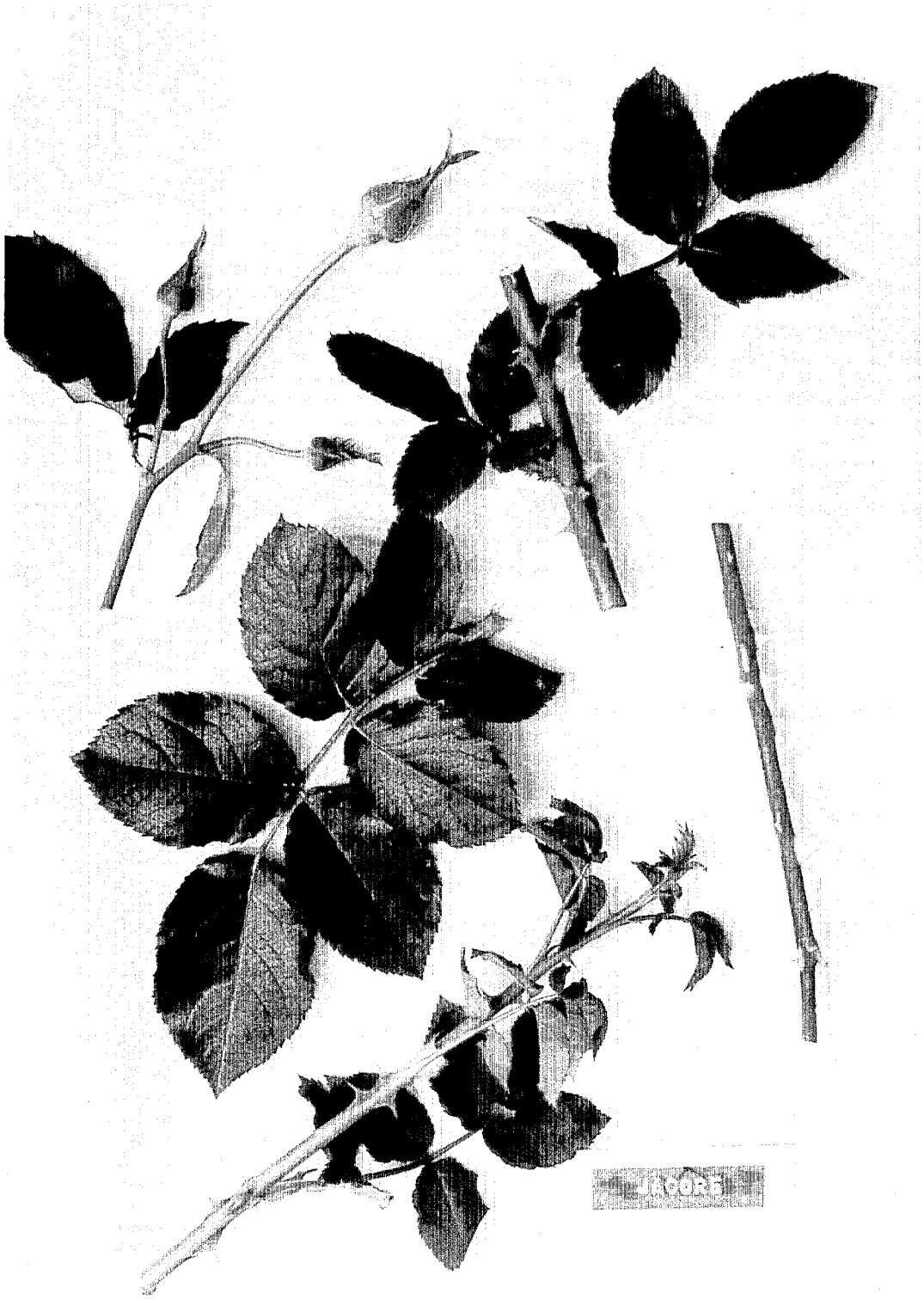
JACORE